United States Patent [19]

Polacco et al.

[11] Patent Number: 5,268,171

[45] Date of Patent: Dec. 7, 1993

[54] METHOD OF ALTERING THE METABOLISM OF A PLANT

[76] Inventors: Joseph C. Polacco, 117 Schweitzer Hall, University of Missouri; Mark A. Holland, 111 Schweitzer Hall, Dept. of Biochemistry, University of Missouri, both of Columbia, Mo. 65211

[21] Appl. No.: 698,597

[22] Filed: May 10, 1991

[51] Int. Cl.$^5$ .................. A01N 63/00; A01C 1/06
[52] U.S. Cl. .................. 424/93 D; 47/57.6
[58] Field of Search .......... 800/200, 205; 47/57.6, 47/57.6; 435/172.3; 935/64; 424/93 D

[56] References Cited

U.S. PATENT DOCUMENTS

| | | | |
|---|---|---|---|
| 4,761,373 | 8/1988 | Anderson et al. | 435/172.3 |
| 4,855,230 | 8/1989 | Lindow | 435/30 |
| 4,940,840 | 7/1990 | Suslow et al. | 800/205 |

OTHER PUBLICATIONS

Corpe, W., "A method for detecting methylotrophic bacteria", J. of Microbiological Methods, vol. 3 (1985) pp. 215-221.
Dumenil, G., et al., "Pigment production by a facultative methylotrophic", Biosis Abstract 84:274150 to Ann. Pharm. Fr., vol. 41 (1983) pp. 427-436.
Joklik, K. and Willett, H., "Zinsser Microbiology", 16th Ed., N.Y., Appleton-Century-Crofts, 1976, p. 142.
Brock, T., "Biology of Microorganisms", 3rd Ed., N.J., Prentice Hall, Inc., 1979, p. 359.
Tsuji, K. et al., "16S Ribosomal RNA Sequence Analysis", Biosis Abstract #90:127321, to J. General Microbiology, vol. 136 (1990) pp. 1-10.
Wood, D., et al., "DNA Hybridization Studies of PPFMs", Biosis Abstract #87:226280, to J. General Microbiology, vol. 133 (1987) pp. 709-720.
Yang, S., et al., "Isolation and Characterization of a PPFM Bacterium", Biosis Abstract #89:339,384, Korean J. Microbiology, vol. 27 (1989) pp. 63-69.
Bass, L., "Physiological and Other Aspects of Seed Presentation", in: Rubenstein, I., et al., The Plant Seed, N.Y., Academic Press, 1979, pp. 152-161.
Curtiss, H. and Barnes, N., "Biology", 5th Ed., N.Y., Worth Publishers, Inc., 1989, p. 643.
Altenbach, S., et al., Plant Molecular Biology, vol. 13 (1989) pp. 513-522.
Vaeck, M., et al., Nature, vol. 328 (1987) pp. 33-37.
Holland et al., Development Genetics, vol. 8 (1987) pp. 375-387.
Hill, H., et al., Phytochemistry, vol. 11, (1972) pp. 9-18.

*Primary Examiner*—David T. Fox
*Assistant Examiner*—Charles Rories
*Attorney, Agent, or Firm*—Reising, Ethington, Barnard, Perry & Milton

[57] ABSTRACT

A method of altering the metabolism of a plant includes the steps of genetically altering at least one commensal bacterium of the plant to alter the level and nature of the enzyme activity produced by the plant. Because of the close relationship between the commensal bacteria and plant with regard to total enzyme activity, and the relationship of total enzyme activity to agronomic production, the present invention provides a mechanism to significantly improve agronomic performance.

3 Claims, 1 Drawing Sheet

METHOD OF ALTERING THE METABOLISM OF A PLANT

This invention was made with Government support under NSF DCB-8718314 and DCB 88-04778 awarded by the National Science Foundation. The Government has certain rights in the invention.

TECHNICAL FIELD

The present invention relates to methods of altering the metabolism of a plant in order to alter the agronomic performance of the host plant. Specifically, the present invention relates to genetically altering seed-transmitted commensal bacteria for the purpose of altering the agronomic performance of the host plant.

BACKGROUND OF THE INVENTION

In the past, a basic assumption of plant biologists and biochemists is that the internal tissues of plants are sterile. Any microbial activity in cell cultures or tissue extracts as attributed to contamination as opposed to indigenous bacteria. Rarely is it considered that the contaminant might have been associated with the plant in nature in a biologically meaningful way. A more pernicious assumption is that if there is no apparent microbial contamination in a culture or extract, then the enzymatic activities present in the plant must be plant activities themselves. That is, all activities related to the plants, such as enzymatic activities, are directly related to indigenous plant enzymes. Applicant has been forced to reconsider these assumptions with the findings that an enzymatic activity in leaf tissue and cell cultures of soybean is of bacterial origin.

Upon applicant's discovery of the commensal bacteria, it still did not remain clear whether one could distinguish bacterial from plant activity in whole tissue assays and whether the bacteria made any contribution to plant metabolism or to what extent the plant influences the metabolism of the bacteria.

Previously, plant production has been altered in various ways. For example, genetic engineers have attempted to modify the genome of plants directly to alter agronomic performance. Of course, classic methods of grafting and cross pollinating plants have been used.

Applicant herein discloses a discovery of commensal bacteria which have a significant contribution to the enzyme activity of the host plant. Further, applicant has further demonstrated that plants can be cured, in whole or in part, of their bacterium and that activation of at least two bacterial enzymes is achieved by the plant's metabolic machinery. Thus, there is a close probability of coadaption and association between the bacterium and its plant host. Utilizing this relationship, applicant will increase the agronomic performance of the plant reintroducing genetically altered or engineered strains into cured plants thus endowing the host plant with improved agronomic performance.

There have been other reports in the literature that biochemical activities in plants may be due to naturally associated non-pathogenic bacteria (1,2,3). It seems that these are treated as exceptional examples of symbiosis and are not taken as indicative of a general biological phenomenon. There is little doubt that many of the activities of microbial commensals associated with plants are insignificant to the plant.

Pink-pigmented, facultative methylotrophs (PPFM's) were first described in connection with plants more than 20 years ago when it was demonstrated that cell cultures of the leafy liverwort Scapania are routinely associated with PPFM's (4). In the years since that time, PPFM's have been isolated for more than 60 species of plants, including both nonvascular and vascular plants, gymnosperms and angiosperms, dicots and monocots (5). These observations have lead to the speculation that the bacteria are universally associated with plants, but the exact nature of the relationships has remained obscure.

The bacteria are seed transmitted and have been seen by electron microscopy to occupy cavities in the cuticle in the leaf tissue (6). Basile et al. has shown that liverworts cultured in the absence of PPFM's require supplementary vitamin B-12 and that vitamin B-12 is produced by the bacteria (7). Although it has long been supposed that plants do not produce vitamin B-12, cobalamin-dependent enzyme activities are known to exist in plants (8,9). It has also recently been reported that plants produce free methanol which suggests that the availability of an exploitable resource for the PPFM is not accessible by other phylloplane bacteria (6).

SUMMARY OF THE INVENTION

In accordance with the present invention, there is provided a method of altering the metabolism of a plant by genetically altering at least one commensal bacterium of the plant to alter total plant enzyme activity and metabolism. By altering the plant's total enzyme activity and metabolism, factors related to agronomic performance of the plant, the agronomic performance will be altered in a positive manner.

FIGURES IN THE DRAWINGS

Other advantages of the present invention will be readily appreciated as the same becomes better understood by reference to the following detailed description when considered in connection with the accompanying drawings wherein:

FIG. 1 shows leaf prints on selective ammonium mineral salts, ATCC Media handbook, #748 medium; and FIG. 2 shows hydrogenase activity of PPFM isolates from four genotypes of soybean.

DETAILED DESCRIPTION OF THE INVENTION

Figure 1:
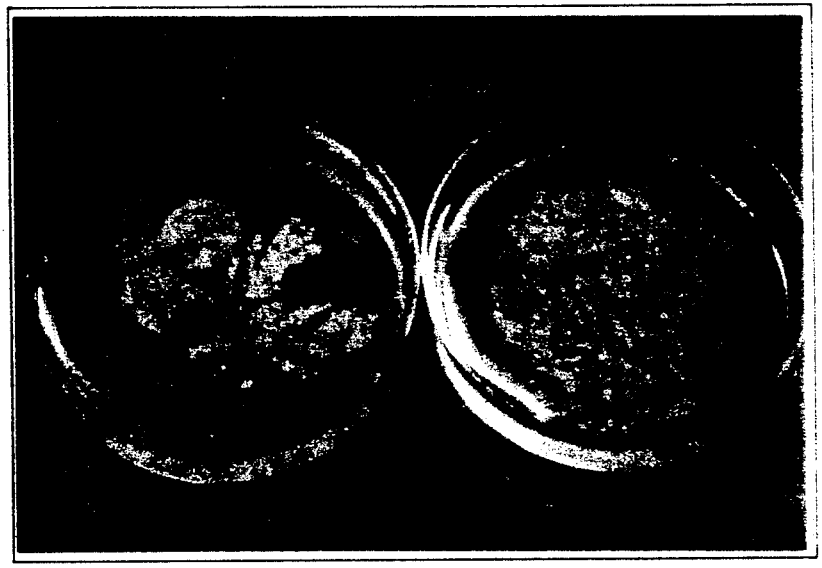

The present invention provides a method of altering the metabolism of a plant by genetically altering at least one commensal bacterium of the plant to alter a total enzyme activity produced by the plant. By altering a total enzyme activity, applicant has recognized as reported herein that certain enzyme activities previously thought to be totally a result of indigenous plant enzymes are actually a mixture of plant enzyme activity combined with the enzyme activity of commensal bacteria. Accordingly, genetic alterations of an enzyme activity of the bacterium of the plant can significantly alter the total enzyme activity produced by the plant. If this total enzyme activity relates to agronomic activity, then the total agronomic performance of the plant can be improved by the genetic alteration of the commensal bacterium therein. This alteration could be an increase or decrease in an enzyme activity dependent upon how the enzyme activity relates to the total agronomic production of the plant. For example, decrease in sucrose synthetase (adenosine diphosphate glucose pyrophosphorylase) reduces starch and raises the sugar content of corn (22).

Applicant has determined that commensal bacteria can be responsible for a significant part of a total enzyme activity of a plant. For example, the experimental data herein demonstrates that the ubiquitous commensal bacterium, *Methylobacterium mesophilicum*, is responsible for a significant part, up to 50%, of the total urease activity of some soybean tissues.

The subject method thusly includes the step of curing the plant, in whole or in part, of the bacterium, and reintroducing genetically altered or engineered strains into the cured plant thus endowing the host plant with improved agronomic performance. In other words, the present invention utilizes a bacterium already known to be compatible with host plants and capable of functioning in host plants to contribute to a total enzyme production of the host plant. By utilizing state of the art genetics and genetic engineering, the present invention will reintroduce the genetically altered or engineered strain of the commensal bacteria back into the cured or partially cured plant thereby effecting a host plant with increased or altered enzyme activity contributing to altered and improved agronomic activity.

The introduction and transfer of the genetically altered or engineered strains can be accomplished by several methods. For example, cured seed can be imbibed in bacterial suspensions. Applicant has shown that this treatment does not reduce germination in normal seeds (unpublished observations). Alternatively, cured scions can be grafted onto bacteria associated stocks pursuant to well known methods practiced in agriculture. Bacterial-associated embryos can be propagated under cell culture isolation that induce plantlet formation. Another method capable of introducing and transferring the commensal bacterium to the host plant is to vacuum infiltrate bacteria into seedlings or somatic embryos. Alternatively, it can be determined whether transmission of marked bacteria is uni-or biparental in crosses of cured X non-cured plants. Finally, soybean cuttings could be rooted in water or nutrient solutions containing bacteria (23).

Various prior art methods of genetically altering bacteria can be used in accordance with the present invention. For example, spontaneous and induced mutants can be recovered and selected for resistance to a series of antibiotics, such as pipericillin, rifampicin, etc. If desired, multiple resistances can be assembled.

An alternate approach for altering the bacteria is to recover bacteria which have acquired promiscuous plasmids bearing drug resistance (gene conferring drug inactivation). This can be accomplished by introduction of plasmid pRK 2013 which encodes kanamycin resistance.

Another method of altering the bacteria is recover bacteria resistant to, or able to inactivate herbicides such as glyphosate and sulfonyl urease which inhibit the 5-enolpyruvylshikimic acid-3-phosphate synthase and acetolactate dehydrogenase, respectively.

Two other methods capable of use with the present invention to alter the bacteria is to recover bacteria which over produce methionine, such as from screens of individuals resistant to methionine analogs or direct screens of over producers and engineering bacterial resistance to natural or synthetic insecticides, such as BT toxin.

Of the above methods, the method of recovering the spontaneous induced mutants or bacteria which acquire promiscuous plasmids allow the following of bacteria in reintroduction and plant-plant transfer experiments. The method of recovering bacteria resistant to herbicides confers resistance to industrial herbicides in the progeny plants. The method of recovering bacteria which over-produce methionine may improve the nutritional content of such factors as soybean protein. For example, it is known from in vitro cotyledon culture and whole plant infusion that methionine supplementation results in soybean seed protein with a high methionine content (24,25). Methionine is a nutritionally limiting amino acid when monogastric animals are fed soybean protein.

Finally, the method of engineering bacteria to produce natural or synthetic insecticides such as BT toxin may make tissues, such as soybean tissues, insect resistant by accumulation of safe insecticides. The *Bacillus thuringenis* bacterium, which produces the BT toxin, can be ingested by animals with no ill effects whereas many insect larva are killed by eating the *B thuringenis* containing leaves.

The above not only illustrates various methods by which the bacterium can be transferred and altered, but also illustrates the utility of the present invention in the agricultural industries.

Applicant has previously described two urease isoenzymes in soybean and the genetics of their tissue-specific expression (10). Developing seeds produce an abundant embryo-specific urease which accumulates to 0.1% of the dry seed weight. Mutants lacking this activity define a single locus Eu1 (11). A second locus, Eu4, controls the expression of a ubiquitous urease which is produced in all tissues and in cell culture, but at much lower levels than the seed isoenzyme (12). Continuing analysis of DNA and protein sequences and restriction fragment length polymorphism segregation are consistent with Eu1 and Eu4 being urease structural genes. Double mutant eu1-sun/eu1-sun, eu4/eu4 plants are, as expected, generally urease-negative but we were surprised to discover that they showed 15-40% wild type activity both in whole tissue assays of callus and in young leaves (unpublished observation) (26). This activity did not appear to be due to "leaky" expression of the eu4 allele since the urease activity in eu4 callus and leaf did not resemble the ubiquitous isozyme in pH preference (Table 1).

In an effort to isolate a microbial contaminant responsible for urease activity, leaf and callus were ground in sterile water and the macerates were streaked on rich (LB) and defined (AMS) media (ATCC Media Handbook formulations #1065 and #784 respectively). All plates showed bacterial growth after several weeks at 28° C. LB plates inoculated with leaf macerate, as expected, showed a variety of bacterial and fungal contaminants. Surprisingly, LB plates inoculated with apparently axenic callus and AMS plates inoculated with either leaf or callus shared a single bacterial contaminant. This pink-pigmented, facultative methylotroph (PPFM) has been assigned to the genus Methylobacterium (13) formerly Pseudomonas (4,5,14) among other designations. Because the taxonomy of the group is confusing, if not confused, applicants have continued to use the descriptive name PPFM for these bacteria. In soybean, it has been reported that PPFM's are present on mature leaves in populations as high as $1 \times 10^5$ cfu per gram fresh weight (J. Dunleavy, unpublished data). In young leaves, applicants have observed as many as $4-5 \times 10^5$ cfu per gram fresh weight. The bacterium is difficult to remove with normal treatments for surface-sterilization, e.g. soaking in 10% bleach and 70% ethanol. While many callus and cell suspension cultures can be found to contain the bacterium, it does not generally overgrow those cultures. Because every leaf and callus sample tested contained the bacterium, applicants examined whether it contributed to urease activity to eu4 tissues.

Table 1 shows the results of biochemical comparisons made among the urease activities in wild type soybean and eu4 mutant tissue, and in free-living cultures of PPFM's isolated from soybean. In every case, the activity present in the eu4 callus and leaves resembled that of the bacterial culture rather than that of the ubiquitous (i.e. wild type) soybean urease isozyme.

To demonstrate that microbial activity was responsible for the urease measured in callus and leaves of the eu4 mutant, applicants attempted to cure these tissues of the bacterium. Callus tissue maintained for three weeks on medium with the antibiotic cefotaxime (100 ug/ml) showed no decrease in growth, but 30% lower urease activity than control callus (Table 2). Soybean seeds were cured of their bacterial commensals by two different heat treatments (15) (cured is defined here as elimination of all or most bacteria), followed by normal germination and growth for two weeks. Heat curing is described in footnotes c and d of Table 2.

The extent to which bacterial populations were reduced by the heat treatments was assessed by pressing the abaxial surfaces of excised leaves onto plates of AMS and/or rich media and incubating them for on week at 28° C. (5). Phylloplane bacteria have been reported to be found in greatest abundance embedded in the cuticle of the abaxial surface of the leaf (6).

FIG. 1 shows one such plate on which PPFM's are growing. The leaf imprinted on the plate on the right was grown from heat-treated seed and shows no growth of PPFM's. The leaf imprinted on the plate on the left was grown from untreated seed and shows PPFM growth. From 70-87.5% of leaves from treated seed showed no growth of PPFM's. Leaves of the same plants were assayed for urease activity and, as seen in Table 2, a reduction in the number of PPFM's in the tissue was correlated with a loss of urease activity. Further supporting the conclusion that PPFM's produce a detectable urease activity in the plant is the observation that dimethylformamide, a gratuitous inducer of urease in lichen (16), induces a chloramphenicol-sensitive increase in ureas activity in both PPFM cultures and in mutant and wild type soybean leaves (Table 2). Because the urease activity in the soybean eu4 mutant more closely resembles that of the free-living bacterium than it does the ubiquitous urease of soybean and because removal of the bacterium from callus and leaf of the mutant results in the loss of urease activity from those tissues, it is concluded that the bacterium is the source of urease activity in the soybean mutant.

In view of the above experiments, it can be concluded that the bacterial commensal on soybean produces a detectable enzymatic activity. The above experiments show that this activity is most apparent against the urease-null background conditioned by a structural gene mutation eu4 in the soybean ubiquitous urease isoenzyme (12). The data show that bacterial urease activity in this mutant can approach 40% of the wild-type activity. Applicant conducted further experiments to show that the PPFM bacteria isolated from a second class of urease-null soybeans are themselves urease-null. This class is identified by two unlinked genetic loci Eu2 and Eu3. Mutation at either of these loci leads to pleiotropic inactivation of both plant urease enzymes. The urease-negative phenotype of bacteria isolated from Eu2 or Eu3 plants can be corrected by supplements of nickel, thereby suggesting that defects in nickel metabolism are the basis for the pleiotropic mutations in soybean.

Soybean produces two distinct urease isozymes and mutations affecting these enzymes fall into three distinct classes (17). Class I and Class III mutations are lesions at the structural gene loci Eu1 and Eu4 of the seed-specific and ubiquitous isozymes, respectively (17). As expected, these mutations result in the loss or alteration of one or the other of the isozymes. Class II mutations exert pleiotropic effects on both isozymes (18). Two unlinked loci Eu2 and Eu3 have been identified by Class II mutations. Homozygous plants with mutations eu2 or eu3-el are completely urease-negative in all tissues (18).

Applicants were the first to find the urease activity produced by PPFM bacteria associated with leaf in studies of the Class III mutant eu4. In this mutant, which produces little or no urease in its leaves or in cell culture, the bacterial urease is readily detected-in some tissues at a high level. It is therefore surprising that no bacterial activity is detectable in tissues of the Class II mutants eu2 and eu3-el. The bacteria are present in these plants in populations as high as those found in wild type soybeans (J. Dunleavy, personal communication, and $3 \times 10^5$ cfu per gram fresh weight by our count). Also, PPFM isolates from the Class II mutants streaked on a urease indicator medium (Difco) showed no urease activity.

There are two possible resolutions to this paradox: 1) bacteria on eu2 or eu3-el plants also carry urease mutations, or 2) the pleiotropic effects of the soybean mutations extend to the bacterial phenotype. Bacteria were isolated from leaves of wild type (cv Williams 82), eu2, eu3-31, and eu4 plants in order to test these alternative possibilities.

Bacteria isolated on a selective medium (AMS (14)) from each of the four genotypes were used to inoculate liquid cultures in Tryptic Soy Broth (Difco). These cultures were incubated overnight at 28° C. and were then assayed for urease activity as described earlier (19). Results of these urease assays are shown in Table 3. The data show that the bacteria isolated from the Class II mutants exhibit low urease activity relative to bacteria from both wild type and eu4 plants. The molecular basis of the Class II mutations is unknown, but applicants have suggested previously (17) that Eu2 and Eu3 most likely encode processing functions essential for the maturation of all urease isozymes.

One likely candidate function is the emplacement of a nickel cofactor on the urease apoenzyme. For this reason, applicants tested the possibility that PPFM's isolated from the Class II mutants might be urease-null because they are effectively nickel-starved.

Liquid cultures in AMS medium of the four PPFM isolates were supplemented with nickel (20) and incubated overnight at 28° C. Urease activities of each isolate were then assayed as before.

Results of this experiment are summarized on Table 4. The data show that the addition of nickel corrects the urease-null phenotype of the PPFM's isolated from Class II mutant plants, suggesting that the pleiotropic mutation in soybean influences the phenotype of the plant's bacterial commensal. Additional evidence that availability of nickel is responsible for the urease-null phenotype of the PPFM's on Class II mutants is the observation that these bacteria are also hydrogenase-deficient. Because hydrogenase, like urease, requires a nickel co-factor for activity, applicants assayed the PPFM isolates for hydrogenase activity by testing their ability to reduce methylene blue dye in an atmosphere of hydrogen by the method of Haugland et al.

Figure 2:
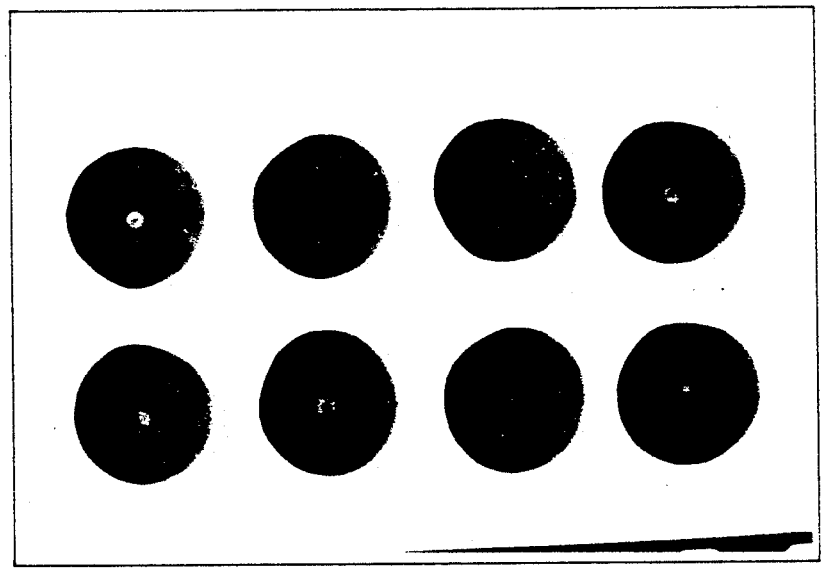

FIG. 2 shows the result of this assay. PPFM's isolated from the Class II mutants are unable to reduce methylene blue unless supplied with nickel.

These results raise several important issues concerning the relationship between the bacterium and its host. In earlier experiments in which the plants PFFM's were cured by heat treatments, it was not necessary to keep treated seed sterile in order to prevent the PPFM's from becoming reestablished on the plant (19). That result suggested that the PPFM's resident on a plant are likely the descendants of seed-borne bacteria, that they are not colonists immigrating by air or water from other plants or from the soil. The results reported here lead to the same conclusion. If the PPFM's are not a mobile population, then it is not reasonable to think that they will be uniformly nickel-starved on the Class II mutants. Indeed, bacteriods of *Bradyhizobium japonicum*, which do invade the plant from the soil are not urease-null in the nodules of the Class II mutants (unpublished observation). Further supporting this idea are SEM micrographs (21) which show the bacteria to be buried in the cuticle of the leaf, not resident on the leaf surface.

Class II mutant plants do contain nickel (18). That bacteria associated with leaves of the Class II mutants can be starved for nickel by the plant requires an explanation. There is no previously described mechanism to explain this result. Finally, the above results indicate that the relationship between plant and PPFM is an intimate one: coadapted and coevolved. Applicants suggest that the bacterium is normally completely dependent on its plant host for its nutritional requirements.

The above data indicate that the commensal bacteria are integral to the metabolism of plants, such as the relationship between the ubiquitous commensal bacterium described above and the host soybean plant. Applicant herein has described specific techniques for altering the bacterium and reintroducing the bacterium into the host for producing improved agronomic performance. It is the close relationship between the plant and the commensal bacterium which allows for the highly expected cooperation and propagation of the altered host plant and seeds.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims the invention may be practiced otherwise than as specifically described.

TABLE 1

Comparisons of urease activities from soybean and PPFM.

| Source of activity | activity at pH6[a] | Percent activity by anti-urease antibody[b] | % inhibition by 0.6 M borate[c] |
|---|---|---|---|
| wild type soybean | 0.78/1.03 = 0.8 | 62 | 100 |
| eu1-sun,eu4 | 1.83/0.94 = 1.7 | 80 | 81 |

TABLE 1-continued

Comparisons of urease activities from soybean and PPFM.

| Source of activity | activity at pH6[a] | Percent activity by anti-urease antibody[b] | % inhibition by 0.6 M borate[c] |
|---|---|---|---|
| double mutant PPFM | 1.49/0.81 = 1.7 | 95 | 85 |

[a]Soybean samples were lyophilized callus tissue, rehydrated in assay buffer (Tris-Malate). Bacterial samples were liquid cultures. Similar activities (1.5–3.0 U) were assayed for each sample as $^{14}CO_2$ released from $^{14}CO$-urea by a method previously described.
[b]Soybean samples were lyophilized callus, ground in assay buffer and clarified by centrifugation; bacterial samples were pelleted cells disrupted in a french press at 18,000 psi. Similar activities (0.5–1.5 U) were reacted in each sample. Non-immune serum was included in the assay as a control. The antibody preparation and details of the experimental method have been described previously.
[c]Soybean samples were discs of tissue punched from leaves. Bacterial samples were liquid cultures. Urease was assayed as described previously except that the assay buffer was Tri-Borate pH 7.0.
[d]This high affinity is corroborated by Western blots, not shown.

TABLE 2

Urease activities in soybean tissues: 1) cured of PPFM's, or 2) treated with an inducer of urease.

| | Tissue | Urease activity (% of control[a]) |
|---|---|---|
| cured with antibiotic | wild type callus | 7.2 |
| | wild type callus on cefotaxime | 7.0 (97%) |
| cured with heat | eu4 leaf[c] | 2.5 |
| | eu4 leaf from treated seed[d] | 0.46 (18%) |
| | eu4 leaf from treated seed[e] | 0.46 (18%) |
| | wild type leaf + chloramphenicol | 100 |
| | wild type leaf + dimethylformamide | 151 (151%) |
| | Wild type leaf + cm = dmf | 114 (114%) |
| induced by dmf[f] | Eu4 leaf + chloramphenicol eu4 | 17 |
| | leaf + dimethylformamide | 31 (182%) |
| | eu4 leaf + cm + dmf | 21 (122%) |
| | PPFM + chloramphenicol | 150 |
| | PPFM + dimethylformamide | 190 (126%) |

[a]Urease activity (nm urea hydrolyzed min) was assayed as described previously.
[b]Callus samples were fresh pieces of tissues, leaf samples were pieces of whole leaf. Activities are expressed per mg fresh weight. Cefotaxime was used at 100 ug per ml.
[c]Dry seed was heated to 40° C. for 48 hours before planting. 87.5% of leaves of plants treated this way showed no growth of PPFM's on AMS medium (see FIG. 1).
[d]Dry seed was heated to 45° C. for 48 hours before planting. 87.5% of leaves of plants treated this way showed no growth of PPFM's on AMS medium (see FIG. 1).
[e]Imbibed seed was heated in a water bath to 52° C. for 10 minutes before planting. 70% of leaves of plants treated this way showed no growth of PPFM's on AMS medium.
[f]Chloramphenicol (cm) was used at 100 ug per ml. Dimethylformamide (dmf) was used at 20 mM. Leaf tissue and bacteria were incubated with these agents for 2 hours at room temperature before being assayed for urease by the standard procedure. Leaf samples were each three disks punched from leaves. Leaf activities are expressed per leaf sample; PPFM activities are per 200 ul of culture.

TABLE 3

Urease activity in PPFM's isolate from different urease soybean plants.

| Source of PPFM | Urease Activity |
|---|---|
| Wild type soybean | 20.1 |
| eu2/eu2 | 3.9 |
| eu3-e1/eu3-e1 | 4.6 |
| eu4/eu4 | 16.3 |

[a]nmol urea hydrolyzed per minutes per unit of optical density at 550 nm of the liquid culture

TABLE 4

Urease activities of PPFM isolates grown with added nickel.

| Source of PPFM | Urease Activity |
|---|---|
| Wild type soybean | 29.9 |
| eu2/eu2 | 35.3 |
| eu3-e1/eu3-e1 | 23.9 |

TABLE 4-continued

Urease activities of PPFM isolates grown with added nickel.

| Source of PPFM | Urease Activity |
|---|---|
| eu4/eu4 | 19.8 |

[a] Nickel was added as "citB". Final concentration of Nickel in the culture medium was 10 μM.
[b] nmol urea hydrolyzed per minute per unit of optical density at 550 nm of the liquid culture.

REFERENCES

1. Libbert, E., Kaiser, W., and Kunert, R., 1969. Phys. Plant. 22:432-439.
2. Hill, H. M. and Rogers, L. J. 1972, Phytochem. 11:9-18.
3. Hayward, A. C. 1974, Ann Rv. Phytopath. 12:87-97.
4. Basile, D. V., Slade, L. L., and Corpe, W. A. 1969, Bull Torr. Bot. Club 96(6):711-714.
5. Corpe, W. A. 1985, J. Micro. Meth. 3:215-221.
6. Corpe, W. A. and Rheem, S., 1989, FEMS Microbiol. Ecol. 62:243-250.
7. Basile, D. V., Basile, M. R., Li, Q., and Corpe, W. A. 1985, The Bryologist 88(2):77-81.
8. Poston, J. M. 1977. Science 195:301-302.
9. Poston, J. M. 1988, Phytochem. 17:401-402.
10. Holland, M. A., Griffin, J. D., Meyer-Bothling, L. E., Polacco, J. C. 1987, Dev. Genet. 8:375-387.
11. Kloth, R>H., polacco, J. C., and Hymowitz, T., 1987, Theor. Appl. Genet. 73:410-418.
12. Polacco, J. C., Judd, A. K., Dybling, J. K. and Cianzio, S. R. 1989. Mol. Gen. Genet. 217:257-262.
13. Green, P. N., and Bousfield, I. J. 1983, Int. J. Syst. Bacteriol, 33(4):875-877.
14. Corpe, W. A. and Basile, D. V. 1982, Deve. Indust. Micro. 23:483-493.
15. Rodriques Perieira, A. S., Houwen, P. J. W., Deurenberg-Vos, H. W. J., and Pey, E. B. F., 1972, Z. Pflanzenphysiol. Bd. 68.S.:170-177.
16. Vicente, C. Nieto, J. M., and Legaz, M. E. 1983., Phys. Plant. 58:325-330.
17. Holland, M. A., Griffin, J. D., Meyer-Bothling, L. E., and Polacco, J. C. 1987, Dev. Genet. 8:375-387.
18. Meyer-Bothling, L. E. Polacco, J. C. and Cianzio, S. R. 1987. Mol. Gen. Genet., 209:432-438.
19. Holland, M. A. and Polacco, J. C. 1991, "Accompanying manuscript".
20. Polacco, J. C. 1977. Plant Physiol. 58:350-357.
21. Corpe, W. A. and Rheem, S. 1989. FEMS Microbiol. Ecol. 62:243-250.
22. Chourey, P. S. and 0. E. Nelson, 1976, The enzymatic deficiency conditioned by the Shrunken-1 mutations in maize, Biochem. Genetics 14:341-343.
23. Torisky, R. S. and Polacco, 1990, Plant. Phys. 94:681-689.
24. Thompson, J. F., Madison, J. T., Waterman, W. A., Muenster, A. M. E., 1981, Phytochemistry 20:941-945.
25. Grabau, L. S. Blevins, D. G., Minor, H. C., 1986, Plant Physiol 82:1013-1018.
26. Polacco, et al, 1989, MGG 217:257-262.

What is claimed is:

1. A method of altering total urease activity in tissue of a soybean plant by altering the fraction of the plant's commensal bacterial population consisting of pink pigmented facultative methylotrophs (PPFM) of the type *Methylobacterium mesophilicum*, which method comprises the steps of curing the plant to reduce its commensal bacterial population, and inoculating the cured plant with *Methylobacterium mesophilicum* bacteria.

2. A method as set forth in claim 1 wherein the PPFM bacteria normally produce up to 50% of the total urease enzyme activity of the host plant.

3. A method as set forth in claim 1 where both the urease activity of the plant and of the PPFM bacteria share a cofactor necessary for the activity of both the plant and bacterial urease enzymes.

* * * * *